(12) United States Patent
Deprez et al.

(10) Patent No.: US 8,962,658 B2
(45) Date of Patent: Feb. 24, 2015

(54) FLUORALKYLCARBONYL-OXADIAZOLES

(71) Applicants: Universite de Droit et de la Sante de Lille 2, Lille (FR); INSERM (Institut National de la Sante et de la Recherche Medicale), Paris Cedex (FR); Institut Pasteur de Lille, Lille Cedex (FR)

(72) Inventors: Benoit Deprez, Lille (FR); Nicolas Willand, Lille (FR); Marion Flipo, Lille (FR); Matthieu Desroses, Orebro (SE); Alain Baulard, Templeuve (BE); Florence Leroux, Templemars (FR)

(73) Assignee: Universite de Droit et de la Sante de Lille 2, Lille (FR)

( * ) Notice: Subject to any disclaimer, the term of this patent is extended or adjusted under 35 U.S.C. 154(b) by 0 days.

(21) Appl. No.: 14/353,899

(22) PCT Filed: Oct. 24, 2012

(86) PCT No.: PCT/EP2012/071084
§ 371 (c)(1),
(2) Date: Apr. 24, 2014

(87) PCT Pub. No.: WO2013/060744
PCT Pub. Date: May 2, 2013

(65) Prior Publication Data
US 2014/0309238 A1   Oct. 16, 2014

(30) Foreign Application Priority Data
Oct. 25, 2011 (EP) .................................. 11370010

(51) Int. Cl.
| | | |
|---|---|---|
| A61K 31/4523 | (2006.01) | |
| C07D 413/14 | (2006.01) | |
| A61K 9/00 | (2006.01) | |
| C07D 413/04 | (2006.01) | |
| C07D 417/14 | (2006.01) | |
| A61K 31/4245 | (2006.01) | |
| A61K 31/454 | (2006.01) | |
| A61K 31/497 | (2006.01) | |
| A61K 31/506 | (2006.01) | |
| A61K 45/06 | (2006.01) | |

(52) U.S. Cl.
CPC .............. *A61K 9/006* (2013.01); *C07D 413/14* (2013.01); *C07D 413/04* (2013.01); *C07D 417/14* (2013.01); *A61K 31/4245* (2013.01); *A61K 31/454* (2013.01); *A61K 31/497* (2013.01); *A61K 31/506* (2013.01); *A61K 45/06* (2013.01)
USPC ............ 514/326; 546/209; 548/131; 514/361
(Continued)

(58) Field of Classification Search
USPC .................... 514/326, 361; 546/209; 548/131
See application file for complete search history.

(56) References Cited

U.S. PATENT DOCUMENTS

| 8,338,599 B2 | 12/2012 | Deprez et al. |
| 2011/0136823 A1 | 6/2011 | Deprez et al. |

FOREIGN PATENT DOCUMENTS

WO   2008/003861   1/2008

OTHER PUBLICATIONS

International Search Report issued May 7, 2013 in International (PCT) Application No. PCT/EP2012/071084.
M. Flipo et al., "Ethionamide Boosters: Synthesis, Biological Activity, and Structure-Activity Relationships of a Series of 1,2,4-Oxadiazole EthR Inhibitors", Journal of Medicinal Chemistry, vol. 54, No. 8, pp. 2994-3010, Apr. 28, 2011.

*Primary Examiner* — Charanjit Aulakh
(74) *Attorney, Agent, or Firm* — Wenderoth, Lind & Ponack, L.L.P.

(57) ABSTRACT

The present invention relates to compounds of Formula (I)

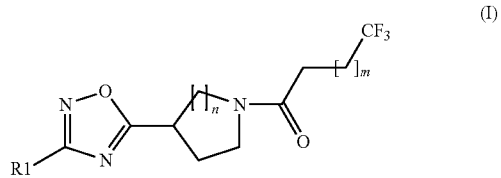

wherein R1 is chosen among the following radicals:

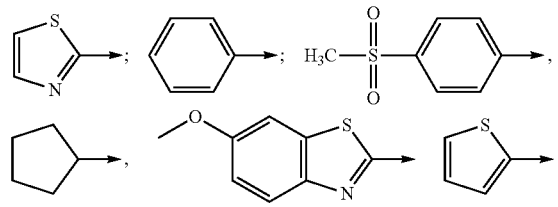

and n=1 or 2 and m=1 or 2 with the proviso that m=2 when R1 is

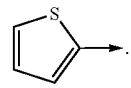

The present invention also relates to the use thereof as drugs, more particularly in the treatment of mycobacterial infections and more particularly in the treatment of tuberculosis.

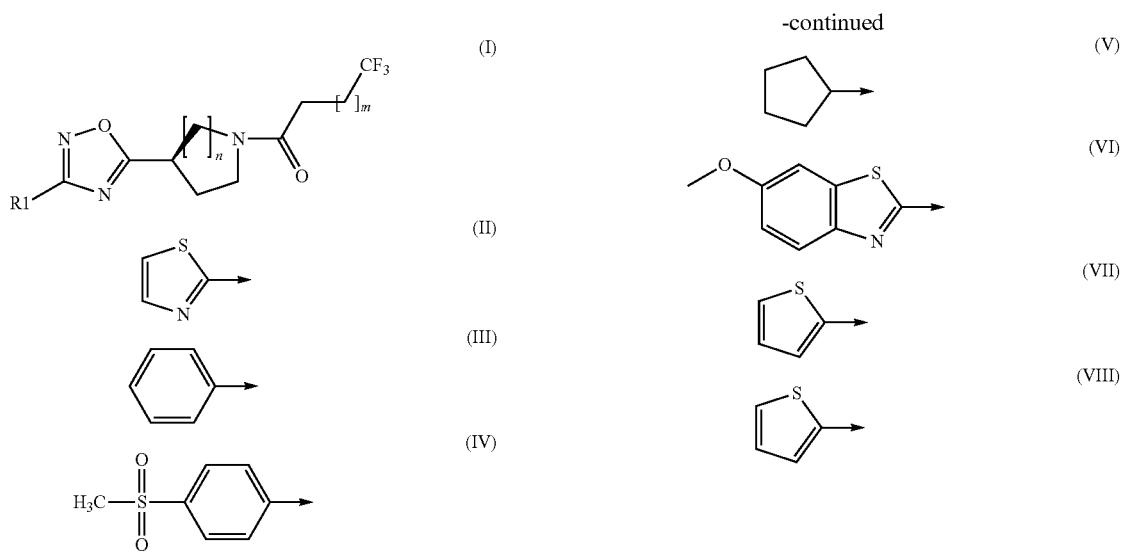
14 Claims, No Drawings

FLUORALKYLCARBONYL-OXADIAZOLES

TECHNICAL FIELD

The present invention relates to compounds having an EthR inhibiting activity. The present invention also relates to the use of said compounds as drugs and to a pharmaceutical composition and products containing said compounds.

PRIOR ART

By killing more than 1.8 million people per year, tuberculosis (TB) represents 2.5% of all preventable deaths globally; this makes it the leading cause of mortality resulting from a bacterial infection. The major obstacles to the global control of this infectious disease include the difficulties to detect and to cure a sufficient number of cases to interrupt transmission. Moreover current estimates suggest that one third of the world's population is infected with the latent form of the pathogen and most of the cases of TB are the result of reactivated latent infection. Nowadays, one observes the development of multidrug-resistant (MDR-TB) and extensively drug-resistant (XDR-TB) strains which more than ever strengthened the need for new drugs.

However drug-resistant tuberculosis is difficult to fight as patients must be treated for two to four years with a cocktail of four to five second-line drugs. These drugs are often associated with serious side effects, which reduce patient compliance and thus lead to high rates of recurrence and mortality. As such, there is strong need for alternative molecules that can improve the efficacy of drugs already used in the clinic.

Ethionamide is a drug widely used for the treatment of MDR-TB. The efficacy of ethionamide in combination with amikacin, pyrazinamide, moxifloxacin has been reconfirmed in mice. As recalled by Lounis et al, this regimen is currently the most potent one against MDR-TB in this in vivo model. Consequently, as the number of MDR and XDR cases is growing worldwide, the importance of ethionamide is steadily increasing. Nevertheless, the prolonged use of ethionamide (750 mg/day for 18 to 24 months) generally causes serious adverse effects, such as gastrointestinal disorders, hepatitis, and various mental disturbances which may drastically reduce patient compliance and thus lead to high rates of recurrence and mortality.

As many anti-TB drugs (hereinafter referred as TB drugs), ethionamide is a prodrug that needs to be transformed inside the mycobacteria to show its antibacterial activity. Bioactivation of ethionamide is catalyzed by the flavin monooxygenase EthA which is under the control of the transcriptional repressor EthR a member of the TetR family of repressors.

It has been shown that the sensitivity of *M. tuberculosis* to ethionamide can be substantially increased in vitro and in vivo by a pharmacological inhibition of EthR. Document WO2008/003861 discloses EthR inhibitors, which can be used as TB drugs. This document discloses 4-4-4-trifluoro-1-[4-(3-thiophen-2-yl-[1,2,4]oxadiazol-5-yl)-piperidin-1-yl] butan-1-one as an EthR inhibitor.

BRIEF SUMMARY

One purpose of the present invention is to provide compounds having an EthR inhibiting activity and thus able to boost the activity of TB drugs.

One other purpose of the present invention is to provide compounds having an improved EthR inhibiting activity.

One other purpose of the present invention is to provide compounds having an EthR activity and having a good biological activity as TB drugs boosters.

One other purpose of the present invention is to provide compounds having an improved microsomal stability (in vitro stability).

One other purpose of the present invention is to provide compounds that can be active in vivo via oral administration.

One other purpose of the present invention is to provide compounds having an EthR inhibiting activity and good physicochemical properties.

The present invention provides compounds of Formula (I)

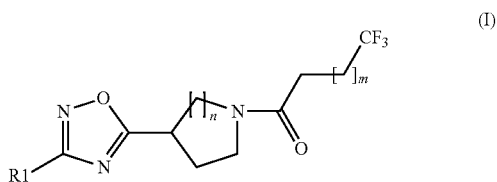

wherein R1 is chosen among the following radicals:

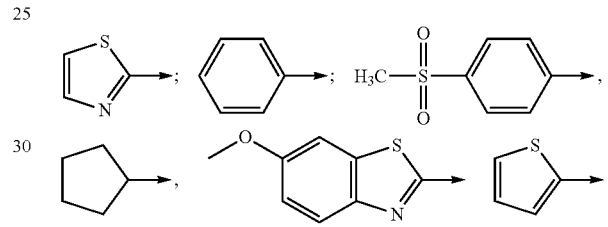

and n=2 or 1 and m=2 or 1 with the proviso that m=2 when R1 is

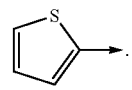

According to the present invention, when R1 is

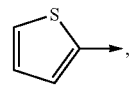

n may be equal to 1 or 2 and m is always equal to 2.

All the afore-mentioned compounds show an inhibiting activity on EthR in cells. More particularly, all of these compounds allow inhibition of *M. tuberculosis* growth in macrophages.

According to a first particular embodiment, n=2. The inventors have shown that when n=2 (cycle is piperidine), the EthR inhibiting activity in cells is improved. Especially, these compounds allow a stronger inhibition of *M. tuberculosis* growth in macrophages in the presence of a TB drug.

According to a second particular embodiment, which may be combined with the former embodiment, m=2. As further explained, the inventors have found that when the side chain is longer and is constituted of 5 carbon atoms, the EthR inhibiting activity is increased. This increased activity is shown on *M. tuberculosis* growth in macrophages in the presence of a TB drug.

According to one other embodiment which may be combined with at least one of the above-mentioned embodiments, R1 is chosen among

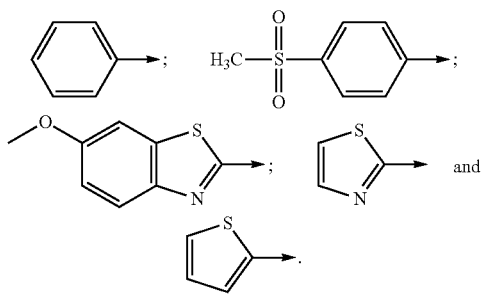

These compounds show particularly good EthR inhibiting activity in macrophages ($EC_{50} \leq 0.5$ µM).

According to one other embodiment, which may be combined with at least one of the first and second embodiments, R1 is chosen among

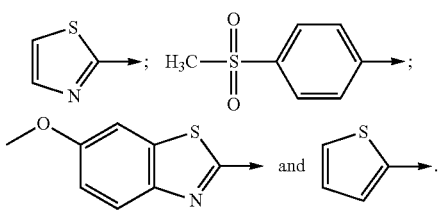

These compounds show a good activity in inhibiting the binding of EthR to its DNA operator ($IC_{50} \leq 3.0$ µM). The inventors have proved that the TB drug boosting activity of these compounds really implies EthR inhibition. According to one other embodiment, which may be combined with the first and/or the second embodiment, R1, is chosen between

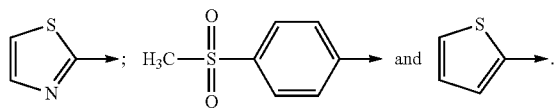

The inventors have discovered that these compounds show a good solubility and a good microsomal stability.

R1 is advantageously chosen among

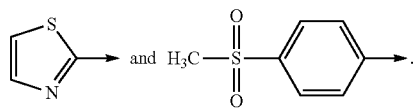

The inventors have shown that these compounds have a good bioavailibility, are drug-like and can be orally administrated. These compounds show a satisfactory in vivo exposure as demonstrated by their AUC. This means that these compounds stay present in organism during a sufficient time period and then can be particularly active even administered at a low dose.

The present invention also relates to the before-mentioned compounds for their use alone or in mixture as a drug.

More particularly, the present invention relates to the previously defined compounds for their use, alone or in mixture, in the treatment of mycobacterial infections, and more particularly in the treatment of tuberculosis.

The present invention also relates to the compounds of the present invention for their simultaneous, separate or sequential use over time with a mixture of at least one antibiotic activable via the EthA enzymatic pathway, in anti-mycobacterial therapy, and more particularly, in anti-tuberculosis therapy.

As regards use of compounds, pharmaceutical composition and product according to the present invention, the antibiotic activable via the EthA enzymatic pathway may be chosen among ethionamide, prothionamide, isoxyl and thiacetazone. However, any other antibiotic activable via the EthA enzymatic pathway may also be used.

The Man skilled in the Art can easily determine whether an antibiotic is activable via the EthA enzymatic pathway by using the method described in "Activation of the prodrug ethionamide is regulated in mycobacteria" 2000 Journal of Biological Chemistry, for instance.

The present invention also relates to a pharmaceutical composition comprising, as an active compound, at least one compound according to the present invention and a pharmaceutically acceptable excipient.

Advantageously, the composition is adapted for an oral administration.

The pharmaceutically acceptable excipient may be hydroxypropyl-β-cyclodextrin. This excipient is non toxic.

The pharmaceutical composition of the invention may also further comprise at least one antibiotic chosen from antibiotics which are activable via the EthA enzymatic pathway.

The present invention also relates to a pharmaceutical composition for its use in the treatment of mycobacterial infections and, more particularly, in the treatment of tuberculosis.

The present invention also relates to a product containing at least one compound according to the invention and at least one antibiotic chosen among antibiotics, that are activable via the EthA enzymatic pathway, as combination products for simultaneous, separate or sequential use over time in general anti-mycobacterial therapy and more particularly in anti-tuberculosis therapy.

According to the present invention, *mycobacterium* infections are infections caused by *Mycobacterium tuberculosis* (*M. tuberculosis*, the major cause of human tuberculosis), *M. bovis*, *M. bovis* BCG, *M. africanum*, *M. canetti*, *M. caprae*, *M. microti*, *M. pinni*, *M. avium*, *M. avium* paratuberculosis, which has been implicated in Crohn's disease in humans and Johne's disease in cattle and sheep, *M. avium silvaticum*, *M. avium* "hominissuis", *M. colombiense*, *M. asiaticum*, *M. gordonae*, *Mycobacterium kansasii* Glade, *M. gastri*, *M. kansasii*, *Mycobacterium nonchromogenicum/terrae* Glade, *M. Hiberniae*, *M. nonchromogenicum*, *M. terrae*, *M. triviale*, *M. ulcerans*, which causes the "Buruli", or "Bairnsdale ulcer", *M. pseudoshottsii*, *M. shottsii*, *M. triplex*, *M. genavense*, *M. florentinum*, *M. lentiflavum*, *M. palustre*, *M. kubicae*, *M. parascrofulaceum*, *M. heidelbergense*, *M. interjectum*, *M. simiae*, *M. cookie*, *M. celatum*, *M. bohemicum*, *M. haemophilum*, *M. malmoense*, *M. szulgai*, *M. leprae*, which causes leprosy, *M. lepraemurium*, *M. lepromatosis*, another (less significant) cause of leprosy, described in 2008, *M. africanum*, *M. botniense*, *M. chimaera*, *M. conspicuum*, *M. doricum*, *M. farcinogenes*, *M. heckeshornense*, *M. intracellulare*, *M. lacus*, *M. marinum*, *M. monacense*, *M. montefiorense*, *M. murale*, *M. nebraskense*, *M. saskatchewanense*, *M. scrofulaceum*, *M. shimoidei*, *M. tusciae* and *M. xenopi* or by a mixture of at least two of the above-mentioned strains.

Tuberculosis is defined as infection caused by *M. tuberculosis*, the major cause of human tuberculosis, *M. bovis, M. bovis* BCG, *M. africanum, M. canetti, M. caprae, M. microti* and *M. pinnipedii* or by a combination of at least two of the above-mentioned strains.

The compounds of the invention may thus be used as a veterinary drug.

DETAILED DESCRIPTION

Experimental Results

As shown in Table 1, introduction of a methylene spacer between the two heteroaromatic rings led to a compound 10 times less active (compound 4). Introduction of a 2-thiazolyl ring (compound 5, $EC_{50}$=0.5 µM) led to a slight decrease of activity. Fusion of the thiazol ring with a methoxy substituted benzene ring (compound 7, $EC_{50}$=0.2 µM) restored activity. 5-thiazolyl was less favourable (compound 6, $EC_{50}$=2.5 µM) as it led to a compound 25 times less active than reference compound 3. The bioisosteric replacement of 2-thienyl ring by phenyl slightly reduced activity (compound 8, $EC_{50}$=0.5 µM). Introduction of basic 6-member-nitrogen rings: pyrazine (compound 9, $EC_{50}$>10 µM), pyrimidine (compound 10, $EC_{50}$=9.0 µM) and pyridine (compounds 11-13) strongly affected activity. Substitutions of the phenyl ring in ortho, meta, and para positions with fluorine and chlorine were as well strongly detrimental for activity except compounds 15 and 19 for which activity was only slightly reduced (compound 15, $EC_{50}$=1.0 µM and compound 19, $EC_{50}$=1.1 µM). Substitution with electron-donating group such as methoxy was also detrimental for activity (compounds 23-25) whereas introduction of a methyl group was more tolerated (compounds 20-22). Substitution with large electron-withdrawing group such as trifluoromethyl group (compounds 26-28) destroyed activity except in para position but led to a compound anyway 5 times less active than non substituted phenyl derivative (compound 8). Hydrogen-bond donor or acceptor functions such as hydroxyl (compound 29) or dimethylamino (compound 30) introduced in para position of the phenyl ring strongly reduced activity. The same result was obtained with a tert-butyl group (compound 31). Replacements by 5- and 6-member aliphatic rings were also tested. Cyclopentyl group led to submicromolar active compound 32 ($EC_{50}$=0.8 µM), whereas higher homologation strongly reduced activity (compound 33, $EC_{50}$=4.0 µM). Accordingly, the inventors have found the importance of 2-thienyl moiety for intracellular activities. However replacement by a non-substituted phenyl ring was tolerated as well as by 2-thiazolyl or 6-methoxy-2-benzothiazolyl heterocycles and cyclopentyl group.

In order to confirm that the boosting activity of submicromolar compounds 5, 7 and 8 ($EC_{50}$≤0.5 µM) is specifically linked to the inhibition of EthR, the inventors tested the capacity of the compounds to inhibit the binding of EthR to its DNA operator, using a Surface Plasmon Resonance (SPR) assay. All tested compounds inhibited binding of EthR to its promoter in a dose dependant manner with $IC_{50}$ in the micromolar range (Table 2).

As shown in Table 2, for a same given radical R1, the EthR inhibiting activity (both $EC_{50}$ and $IC_{50}$) of the compounds comprising a 6-member ring is higher than the activity of the compounds comprising a 5-member ring (see compounds 3 and 2, 5 and 41 and 44 and 43, for example).

Some of the compounds displaying $IC_{50}$<3 µM were further evaluated for their solubility and microsomal stability. Whereas all compounds are drug like in compliance with Lipinski and Veber's rules, they present significantly different physicochemical and pharmacokinetic properties. The most lipophilic compound (compound 7, clogP=3.22) was also the less soluble (solubility=6 µg/mL). Conversely, the less lipophilic derivative (compound 5, clogP=1.61) appeared to be the most soluble analogue in the 1,2,4-oxadiazole series (solubility=300 µg/mL). Compound 3 ($CI_{int}$=213 µL·min$^{-1}$·mg$^{-1}$) was far less stable than the (R)-1,3-pyrrolidine derivative in mouse microsomes (compound 2, $CI_{int}$=4 µL·min$^{-1}$·mg$^{-1}$). Replacement of 2-thienyl by 2-thiazolyl enhanced microsomal stability (compound 5, $CI_{int}$=37 µL·min$^{-1}$·mg$^{-1}$). Compound 41 which combine 2-thiazolyl and (R)-1,3-pyrrolidine as key modifications was synthesized. Unfortunately, this compound was ten times less active than the two parent compounds which disqualified it for further ADME studies. Conversely, compound 7, which had promising activities, was unfortunately poorly soluble (6 µg/mL) and stable on microsomes ($CI_{int}$=197 µL·min$^{-1}$·mg$^{-1}$). The in vivo pharmacokinetic parameters of the most stable compounds 2 and 5 were then evaluated in mice by oral administration at 20 mg/kg using DMSO as vehicle. Area under the concentration-time curve (AUC) for compounds 2 and 5 were respectively 0.1 µg·mL$^{-1}$·h and 73.5 µg·mL$^{-1}$·h (Table 2). Despite its good microsomal stability, compound 2 displays a poor in vivo exposure maybe due to low absorption after oral administration. At this stage, compound 5 presented the best compromise in terms of activity, solubility, microsomal stability and mouse exposure. In order to reduce potential toxicity inherent to repeated in vivo administration of DMSO, a more convenient aqueous hydroxypropyl-β-cyclodextrin-based formulation was tested and AUC for compound 5 reached 100.5 µg·mL$^{-1}$·h (Table 2).

As also shown in Table 2, surprisingly, the extension of the 4,4,4-trifluorobutyryl chain length by one supplementary methylene spacer give rise to compounds having an increased EthR activity (both $EC_{50}$ and $IC_{50}$). For example, compound 42, 45, 43 and 44 show an increased EthR inhibiting activity compared to compound 5, 8, 2 and 3 respectively.

The crystal structure of EthR in complex with compound 42 may explain these properties. The above-mentioned crystal structure (results not shown) shows a network of hydrogen bond involving Asn179. The improved functional activity of compound 42 is probably due to better van der Waals interactions along the surface, especially between trifluoro-aliphatic chain and the hydrophobic bottom pocket composed with Trp145, Trp138, Phe184, and Glu180.

The lengthening of the 4,4,4-trifluorobutyryl chain was achieved according to Scheme 1 by coupling the free piperidine with 5,5,5-trifluoropentanoic acid. Compound 42 and 46 also proved to have good physicochemical and pharmacokinetic properties including high solubility in PBS (phosphate buffered saline) aqueous buffers (410 µg/mL and 80 µg/mL, respectively), and fairly good stability in mouse liver microsomes with an intrinsic clearance equal to 15 µL·min$^{-1}$·mg$^{-1}$ and 14 µL·min$^{-1}$·mg$^{-1}$, respectively (Table 2).

Compound 42 was formulated in hydroxypropyl-β-cyclodextrin aqueous solution and administered to mice as a single oral dose of 20 mg/kg. The AUC for this compound reached the reasonable value of 98.6 µg·mL$^{1}$·h·

EXPERIMENTS

General Information. NMR spectra were recorded on a Bruker DRX-300 spectrometer. Chemical shifts are in parts per million (ppm). The assignments were made using one dimensional (1D)$^{1}$H and $^{13}$C spectra and two-dimensional (2D) HSQC and COSY spectra. Mass spectra were recorded with a LC-MSMS triple-quadrupole system (Varian 1200 ws)

or a LCMS (Waters Alliance Micromass ZQ 2000). LCMS analysis was performed using a $C_{18}$ TSK-GEL Super ODS 2 µm particle size column, dimensions 50×4.6 mm. A gradient starting from 100% $H_2O$/0.1% formic acid and reaching 20% $H_2O$/80% $CH_3CN$/0.08% formic acid within 10 min at a flow rate of 1 mL/min was used. Preparative HPLC were performed using a Varian PRoStar system using an OmniSphere 10 Column $C_{18}$ 250×41.4 mm Dynamax from Varian, Inc. A gradient starting from 20% $CH_3CN$/80% $H_2O$/0.1% formic acid and reaching 100% $CH_3CN$/0.1% formic acid at a flow rate of 80 mL/min or 20% MeOH/80% $H_2O$/0.1% formic acid reaching 100% MeOH/0.1% formic acid was used. Purity (%) was determined by Reversed Phase HPLC, using UV detection (215 nm) and all compounds showed purity greater than 95%. Melting points were determined on a Büchi B-540 apparatus and are uncorrected. All commercial reagents and solvents were used without further purification.

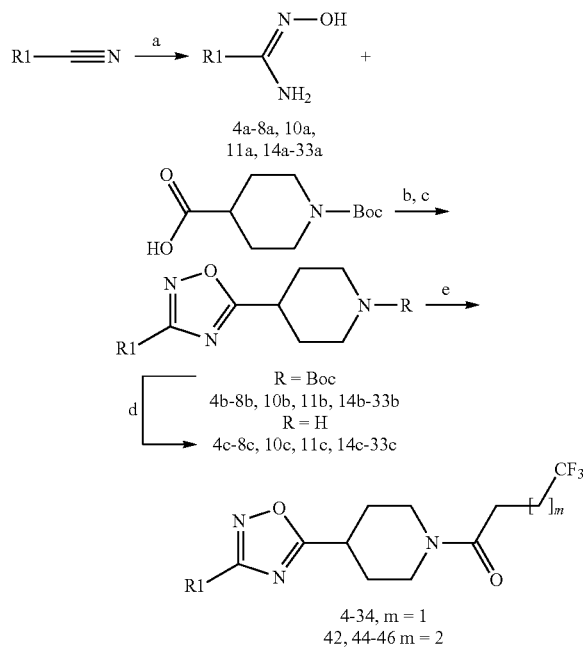

Reagents and reaction conditions: (a) 1.5 eq. $NH_2OH.HCl$, 1.6 eq. DIEA, EtOH, reflux; (b) 1 eq. Boc-isonipecotic acid, 1.1 eq. HBTU, 3 eq. DIEA, DMF, RT, 2 h to overnight; (c) DMF, 120° C., 4 h to 24 h; (d) 5 eq. HCl 4N dioxane, RT, 4 h to overnight; (e) 1.3 eq. 4,4,4-trifluorobutyric acid or 1.3 eq. 5,5,5-trifluoropentanoic acid, 1.3 eq. EDCI, 0.3 eq. HOBt, 4 eq. DIEA, DMF, RT, overnight.

General Procedure for synthesis of amidoximes (4a, 7a, 8a, 10a, 11a, 14a-33a). Carbonitrile (1 equiv), hydroxylamine chloride (1.5 equiv) and DIEA (1.6 equiv) were mixed in absolute EtOH (1 M). The reaction mixture was refluxed until all the nitrile was consumed (TLC or LCMS control) and then the solvent was evaporated under reduce pressure. The residue was dissolved in AcOEt, washed twice with water and once with brine. The organic layer was dried over $MgSO_4$ and then evaporated under reduced pressure.

Synthesis of 1,3-thiazole-2-amidoxime (5a). Hydroxylamine hydrochloride (9.03 g, 130 mmol) was added to a solution of 1,3-thiazole-2-carbaldehyde (14.71 g, 130 mmol) and pyridine (10.5 mL, 130 mmol) in DCM (100 mL). The reaction mixture was stirred overnight at room temperature and then washed twice with water. The organic layer was dried over $MgSO_4$ and then evaporated under reduced pressure to give 15.26 g of 1,3-thiazole-2-carbaldehyde oxime (yield 92%). 1,3-thiazole-2-carbaldehyde oxime (15.23 g, 119 mmol, 1 equiv) was dissolved in 80 mL of dioxane and then TEA (41.4 mL, 2.5 equiv) was added. The reaction mixture was cooled to 0° C. and then trifluoroacetic anhydride (18.3 mL, 1.1 equiv) was added dropwise to the reaction. The solution was stirred overnight at room temperature and then evaporated. The residue was dissolved in DCM and then washed twice with water. The organic layer was dried over $MgSO_4$ and then evaporated under reduced pressure to give 1,3-thiazole-2-carbonitrile. This compound was used in the next step without further purification. 1,3-thiazole-2-carbonitrile (13.11 g, 119 mmol, 1 equiv), hydroxylamine hydrochloride (12.4 g, 1.5 equiv) and DIEA (33 mL, 1.6 equiv) were mixed in absolute EtOH (150 mL). The reaction mixture was refluxed 4 h and then the solvent was evaporated under reduced pressure. The residue was dissolved in AcOEt, washed twice with water and once with brine. The organic layer was dried over $MgSO_4$ and then evaporated under reduced pressure to give 15.86 g of 1,3-thiazole-2-amidoxime (yield 93% over two steps).

Synthesis of 1,3-thiazole-5-amidoxime (6a). Hydroxylamine hydrochloride (3.07 g, 44 mmol) was added to a solution of 1,3-thiazole-5-carbaldehyde (5 g, 44 mmol) and pyridine (3.7 mL) in DCM (25 mL). The reaction mixture was stirred overnight at room temperature and then washed once with water. The product was recovered by filtration to give 5.23 g of 1,3-thiazole-5-carbaldehyde oxime (yield 92%). 1,3-thiazole-5-carbaldehyde oxime (2.5 g, 19.5 mmol, 1 equiv) was dissolved in 12 mL of dioxane and then TEA (6.8 mL, 2.5 equiv) was added. The reaction mixture was cooled to 0° C. and then trifluoroacetic anhydride (3.0 mL, 1.1 equiv) was added dropwise to the reaction. The solution was stirred overnight at room temperature and then 1.1 equivalent of trifluoroacetic anhydride was added to complete the reaction. The solution was stirred overnight at room temperature and then evaporated. The residue was dissolved in DCM and then washed five times with water. The organic layer was dried over $MgSO_4$ and then evaporated under reduced pressure to give 1.25 g of 1,3-thiazole-5-carbonitrile (Yield 58%). 1,3-thiazole-5-carbonitrile (1 g, 9.08 mmol, 1 equiv), hydroxylamine hydrochloride (0.95 g, 1.5 equiv) and DIEA (2.5 mL, 1.6 equiv) were mixed in absolute EtOH (30 mL). The reaction mixture was refluxed 5 h and then the solvent was evaporated under reduced pressure. The residue was dissolved in AcOEt, washed twice with water and once with brine. The organic layer was dried over $MgSO_4$ and then evaporated under reduced pressure to give 940 mg of 1,3-thiazole-5-amidoxime (yield 72%).

General Procedure for synthesis of 1,2,4-oxadiazole (4b-8b, 10b, 11 b, 14b-33b). 1-Boc-piperidine-4-carboxylic acid (10 mmol, 1 equiv), HBTU (1.1 equiv) and DIEA (3 equiv) were dissolved in DMF (15 mL). The solution was stirred 5 min and then the amidoxime (4a-8a, 10a, 11a, 14a-33a) (1 equiv) was added. The reaction mixture was stirred at room temperature 2 h to overnight and then poured in 50 mL of water. The reaction mixture produced a thick crystalline slurry. The product was recovered by filtration and washed with water. Compounds 4b, 6b, and 29b did not precipitate in water. The product was extracted 3 times with AcOEt and then the organic layers were joined, washed twice with saturated aqueous $NaHCO_3$ and once with brine, then dried over $MgSO_4$ and evaporated under reduced pressure.

The solid obtained was dissolved in DMF (15 mL) and then the reaction mixture was heated at 120° C. for 4 to 24 h. The solvent was removed under vacuum and the residue was dissolved in AcOEt. The organic layer was washed twice with HCl 1N, twice with saturated aqueous $NaHCO_3$ and once with brine, then dried over $MgSO_4$ and evaporated under reduced pressure.

General Procedure for deprotection step (4c-8c, 10c, 11c, 14c-33c). Boc intermediates (4b-8b, 10b, 11 b, 14b-33b) were dissolved in dioxane (1 M) and HCl 4N solution in dioxane (5 equiv) was added. The reaction mixture was stirred at room temperature 4 h to overnight. The product was recovered by filtration and then washed with petroleum ether.

Compounds 4c, 32c and 33c did not precipitate. The dioxane was removed under reduced pressure and then the residue was dissolved in water and washed twice with AcOEt. The pH of the aqueous phase was adjusted to 10 with saturated aqueous $K_2CO_3$ and then the product was extracted 3 times with AcOEt. The organic phases were joined, washed once with brine, then dried over $MgSO_4$ and evaporated under reduced pressure.

Compounds 9c, 12c, 13c and 34c were purchased from Peakdale.

General Procedure for coupling (4-34). 4,4,4-trifluorobutyric acid (1.3 equiv), EDCI (1.3 equiv), HOBt (0.3 equiv) and DIEA (4 equiv) were mixed in DMF (2 mL) for 5 minutes. Piperidine intermediate (0.8 mmol, 1 equiv) was added with 3 mL of DMF. The reaction mixture was stirred overnight at room temperature and then evaporated under reduced pressure and purified by preparative HPLC.

4,4,4-Trifluoro-1-[4-(3-thiazol-2-yl-1,2,4-oxadiazol-5-yl)-piperidin-1-yl]-butan-1-one (5). Yield 55%; $^1$H NMR ($CDCl_3$) δ 8.07 (d, J=3.3 Hz, 1H), 7.60 (d, J=3.3 Hz, 1H), 4.49-4.54 (m, 1H), 3.91-3.96 (m, 1H), 3.27-3.38 (m, 2H), 2.98-3.07 (m, 1H), 2.50-2.64 (m, 4H), 2.11-2.28 (m, 2H), 1.87-2.09 (m, 2H); $^{13}$C NMR (CDCl3): δ 181.78, 168.10, 164.03, 153.75, 145.01, 127.04 (q, J=275 Hz), 122.56, 44.39, 40.99, 34.30, 29.59 (q, J=30 Hz), 29.33, 28.80, 25.93 (q, J=2.8 Hz). $t_R$ LCMS 4.8 min. Purity >99%; MS $[M+H]^+$ m/z 361.

4,4,4-Trifluoro-1-{4-[3-(6-methoxy-benzothiazol-2-yl)-1,2,4-oxadiazol-5-yl]-piperidin-1-yl}-butan-1-one (7). Yield 47%; $^1$H NMR ($CDCl_3$) δ 8.13 (d, J=9.0 Hz, 1H), 7.40 (d, J=2.4 Hz, 1H), 7.17 (dd, J=9.0 Hz, J=2.4 Hz, 1H), 4.52-4.57 (m, 1H), 3.93-4.00 (m, 1H), 3.93 (s, 3H), 3.25-3.40 (m, 2H), 2.97-3.05 (m, 1H), 2.45-2.65 (m, 4H), 2.19-2.28 (m, 2H), 1.94-2.07 (m, 2H); $^{13}$C NMR (CDCl3): δ 181.96, 168.11, 164.57, 159.22, 150.82, 148.04, 137.15, 127.03 (q, J=275 Hz), 125.40, 117.11, 103.62, 55.88, 44.45, 41.06, 34.45, 29.60 (q, J=29 Hz), 29.38, 28.85, 25.95 (q, J=2.8 Hz). $t_R$ LCMS 6.3 min. Purity >99%; MS $[M+H]^+$ m/z 441.

4,4,4-Trifluoro-1-[4-(3-phenyl-1,2,4-oxadiazol-5-yl)-piperidin-1-yl]-butan-1-one (8). Yield 43%; $^1$H NMR ($CDCl_3$) δ 8.08 (dd, J=7.8 Hz, J=1.8 Hz, 2H), 7.46-7.53 (m, 3H), 4.48-4.53 (m, 1H), 3.90-3.95 (m, 1H), 3.27-3.35 (m, 2H), 3.00-3.09 (m, 1H), 2.51-2.63 (m, 4H), 2.18-2.23 (m, 2H), 1.91-2.02 (m, 2H); $^{13}$C NMR (CDCl3): δ 180.65, 168.34, 168.08, 131.29, 128.90, 127.43, 126.65, 127.08 (q, J=275 Hz), 44.43, 41.02, 34.22, 29.61 (q, J=29 Hz), 29.49, 28.90, 25.95 (q, J=2.9 Hz). $t_R$ LCMS 6.3 min. Purity >99%; MS $[M+H]^+$ m/z 354.

1-[4-(3-Cyclopentyl-1,2,4-oxadiazol-5-yl)-piperidin-1-yl]-4,4,4-trifluoro-butan-1-one (32). Yield 45%; $^1$H NMR ($CDCl_3$) δ 4.43-4.48 (m, 1H), 3.84-3.89 (m, 1H), 3.12-3.29 (m, 3H), 2.91-3.00 (m, 1H), 2.42-2.61 (m, 4H), 1.97-2.16 (m, 4H), 1.63-1.92 (m, 8H); $^{13}$C NMR (CDCl3) δ 180.15, 173.91, 167.96, 127.02 (q, J=275 Hz), 44.37, 40.96, 36.50, 34.12, 31.26, 29.49 (q, J=29 Hz), 29.39, 28.82, 25.78, 25.44. $t_R$ LCMS 5.7 min. Purity >99%; MS $[M+H]^+$ m/z 346.

4,4,4-trifluoro-1-{4-[3-(4-methanesulfonylphenyl)-1,2,4-oxadiazol-5-yl]piperidin-1-yl}butan-1-one (34). Yield 67%; $^1$H NMR ($CDCl_3$) δ 8.31 (d, J=8.5 Hz, 2H), 8.09 (d, J=8.5 Hz, 2H), 4.52-4.57 (m, 1H), 3.93-3.98 (m, 1H), 3.29-3.38 (m, 2H), 3.12 (s, 3H), 2.99-3.09 (m, 1H), 2.49-2.67 (m, 4H), 2.20-2.30 (m, 2H), 1.86-2.06 (m, 2H). $t_R$ LCMS 5.3 min. Purity >99%; MS $[M+H]^+$ m/z 432.

4,4,4-trifluoro-1-[(3R)-3-[3-(1,3-thiazol-2-yl)-1,2,4-oxadiazol-5-yl]pyrrolidin-1-yl]butan-1-one (41). (R)—N—Boc-pyrrolidine-3-carboxylic acid (700 mg, 3.25 mmol, 1.1 equiv), HBTU (1.23 g, 1.1 equiv) and DIEA (1.53 mL, 3 equiv) were dissolved in DMF (15 mL). The solution was stirred 5 min and then 1,3-thiazole-2-amidoxime (5a) (422 mg, 2.95 mmol, 1 equiv) was added. The reaction mixture was stirred overnight at room temperature and then evaporated under reduced pressure. The residue was dissolved in AcOEt, washed twice with saturated aqueous $NaHCO_3$, once with brine, then dried over $MgSO_4$ and evaporated under reduced pressure. The residue was dissolved in 15 mL of DMF and then heated at 110° C. for 7 h. The solvent was removed under vacuum and the residue was dissolved in AcOEt. The organic layer was washed once with HCl 1N, once with saturated aqueous $NaHCO_3$ and once with brine, then dried over $MgSO_4$ and evaporated under reduced pressure. The obtained product was used in the next step without further purification. Boc intermediate was dissolved in dioxane (10 mL) and HCl 4N solution in dioxane (6 mL) was added. The reaction mixture was stirred overnight at room temperature and then the product was recovered by filtration and washed with petroleum ether to give 5-[(3R)-pyrrolidin-3-yl]-3-(1,3-thiazol-2-yl)-1,2,4-oxadiazole (yield 66% over two steps). 4,4,4-trifluorobutyric acid (1.3 equiv), EDCI (1.3 equiv), HOBt (0.4 equiv) and DIEA (4 equiv) were mixed in DMF (2 mL) for 5 minutes. 5-[(3R)-pyrrolidin-3-yl]-3-(1,3-thiazol-2-yl)-1,2,4-oxadiazole (0.62 mmol, 1 equiv) was added with 3 mL of DMF. The reaction mixture was stirred overnight at room temperature and then evaporated under reduced pressure and purified by preparative HPLC. Beige powder; Yield 33%; $^1$H NMR ($CDCl_3$) δ 8.02-8.00 (m, 1H), 7.57-7.60 (m, 1H), 3.89-4.03 (m, 2H), 3.69-3.87 (m, 2H), 3.53-3.65 (m, 1H), 2.38-2.55 (m, 6H); $^{13}$C NMR ($CDCl_3$) cis/trans isomer mixture (60 isomer A/40 isomer B); isomer A δ 180.31, 168.50, 163.98, 153.53, 144.99, 126.94 (q, J=276 Hz), 122.87, 49.24, 45.52, 35.03, 29.05 (q, J=29 Hz), 28.86, 27.07 (q, J=3 Hz); isomer B δ 179.84, 168.31, 163.98, 153.38, 144.94, 126.92 (q, J=276 Hz), 122.81, 49.43, 45.25, 36.82, 30.28, 29.05 (q, J=29 Hz), 27.24 (q, J=3 Hz). $t_R$ LCMS 4.6 min. Purity >99%; MS $[M+H]^+$ m/z 347.

5,5,5-Trifluoro-1-[4-(3-thiazol-2-yl-1,2,4-oxadiazol-5-yl)-piperidin-1-yl]-pentan-1-one (42). 5,5,5-Trifluoropentanoic acid (1.3 equiv), EDCI (1.3 equiv), HOBt (0.3 equiv) and DIEA (4 equiv) were mixed in DMF (40 mL) for 5 minutes. 4-(3-thiazol-2-yl-[1,2,4]oxadiazol-5-yl)-piperidine hydrochloride (5c) (8.18 g, 30 mmol, 1 equiv) was added with 20 mL of DMF and the reaction mixture was stirred overnight at room temperature and then evaporated under reduced pressure. The residue was dissolved in AcOEt and then washed twice with saturated aqueous $NaHCO_3$, twice with HCl 1N and once with brine, then dried over $MgSO_4$ and evaporated under reduced pressure. The residue was purified by chromatography on silica gel (DCM/MeOH 100-0 to 98.5-1.5) and then recrystallized in a mixture of isopropanol and diisopropyl ether. Yield 62%; $^1$H NMR ($CD_2Cl_2$) δ 8.06 (d, J=3.0 Hz, 1H), 7.65 (d, J=3.0 Hz, 1H), 4.51-4.55 (m, 1H), 3.90-3.95 (m, 1H), 3.22-3.39 (m, 2H), 2.91-2.98 (m, 1H), 2.44 (t, J=7.2 Hz, 2H), 2.15-2.27 (m, 4H), 1.83-2.01 (m, 4H); $^{13}$C NMR (CDCl$_3$) δ 182.06, 169.56, 163.97, 154.00, 144.95, 127.37 (q, J=275 Hz), 122.66, 44.33, 40.60, 34.43, 32.97 (q, J=29 Hz), 31.34, 29.44, 28.90, 17.52. mp 75.6-76.3° C.; $t_R$ LCMS 6.1 min. Purity >99%; MS [M+H]$^+$ m/z 375.

5,5,5-trifluoro-1-[(3R)-3-[3-(thiophen-2-yl)-1,2,4-oxadiazol-5-yl]pyrrolidin-1-yl]pentan-1-one (43). (R)—N—Boc-pyrrolidine-3-carboxylic acid (4.65 mmol, 1 equiv), HBTU (1.1 equiv) and diisopropylethylamine (2.5 equiv) were dissolved in dimethylformamide (10 mL). The solution was stirred five minutes then thiophene-2-amidoxime (1 equiv) was added. The reaction mixture was stirred overnight at room temperature then evaporated under reduced pressure. The residue was dissolved in AcOEt and washed twice with saturated aqueous NaHCO3 and once with brine, then dried over MgSO4 and evaporated under reduced pressure. The residue was dissolved in 10 mL of DMF then heated at 120° C. for 9 hours. The solvent was removed under vacuum and the residue was dissolved in AcOEt. The organic layer was washed once with HCl 1N, once with saturated aqueous NaHCO3 and once with brine, then dried over MgSO4 and evaporated under reduced pressure. The obtained product was used in the next step without further purification. Boc intermediate was dissolved in dioxane (5 mL) and HCl 4N solution in dioxane (5 equiv) was added. The reaction mixture was stirred overnight at room temperature then evaporated under reduced pressure. The residue was dissolved in water then washed once with diethyl ether. The pH of the aqueous phase was adjusted to 8 with saturated aqueous K2CO3 then the product was extracted 3 times with AcOEt. The organic phases were joined, washed once with brine, then dried over MgSO4 and evaporated under reduced pressure to give 5-(R)-Pyrrolidin-3-yl-3-thiophen-2-yl-1,2,4-oxadiazole (yield 74% over two steps). 5,5,5-Trifluoropentanoic acid (1.3 equiv), EDCI (1.3 equiv), HOBt (0.3 equiv) and diisopropylethylamine (4 equiv) were mixed in DMF (2 mL) for 5 minutes. 5-(R)-Pyrrolidin-3-yl-3-thiophen-2-yl-1,2,4-oxadiazole (0.85 mmol, 1 equiv) was added with 3 mL of DMF. The reaction mixture was stirred overnight at room temperature and then evaporated under reduced pressure and purified by preparative HPLC. Yield 60%; $^1$H NMR (CDCl$_3$) δ 7.77-7.80 (m, 1H), 7.51-7.54 (m, 1H), 7.15-7.19 (m, 1H), 3.90-4.04 (m, 2H), 3.70-3.85 (m, 2H), 3.57-3.64 (m, 1H), 2.35-2.52 (m, 4H), 2.18-2.30 (m, 2H), 1.94-2.02 (m, 2H). $t_R$ LCMS 5.4 min. Purity >99%; MS [M+H]$^+$ m/z 360.

5,5,5-trifluoro-1-{4-[3-(thiophen-2-yl)-1,2,4-oxadiazol-5-yl]piperidin-1-yl}pentan-1-one (44). 5,5,5-Trifluoropentanoic acid (1.3 equiv), EDCI (1.3 equiv), HOBt (0.3 equiv) and diisopropylethylamine (4 equiv) were mixed in DMF (2 mL) for 5 minutes. 4-[(3-(thien-2-yl)-1,2,4-oxadiazol-5-yl]-piperidine (0.85 mmol, 1 equiv) was added with 3 mL of DMF. The reaction mixture was stirred overnight at room temperature and then evaporated under reduced pressure and purified by preparative HPLC. Yield 83%; $^1$H NMR (CD$_2$Cl$_2$) δ 7.80 (dd, J=1.2 Hz, J=3.6 Hz, 1H), 7.56 (dd, J=1.2 Hz, J=5.0 Hz, 1H), 7.19 (dd, J=3.6 Hz, J=5.0 Hz, 1H), 4.48-4.55 (m, 1H), 3.87-3.95 (m, 1H), 3.19-3.33 (m, 2H), 2.89-3.00 (m, 1H), 2.44 (t, J=7.3 Hz, 2H), 2.15-2.31 (m, 4H), 1.86-1.96 (m, 4H). $t_R$ LCMS 6.1 min. Purity >99%; MS [M+H]$^+$ m/z 374.

5,5,5-trifluoro-1-[4-(3-phenyl-1,2,4-oxadiazol-5-yl)piperidin-1-yl]pentan-1-one (45). 5,5,5-Trifluoropentanoic acid (1.3 equiv), EDCI (1.3 equiv), HOBt (0.3 equiv) and diisopropylethylamine (4 equiv) were mixed in DMF (2 mL) for 5 minutes. 4-(3-Phenyl-[1,2,4]oxadiazol-5-yl)-piperidine hydrochloride (8c) (0.85 mmol, 1 equiv) was added with 3 mL of DMF. The reaction mixture was stirred overnight at room temperature and then evaporated under reduced pressure and purified by preparative HPLC. Yield 79%; $^1$H NMR (CDCl$_3$) δ 8.06-8.09 (m, 2H), 7.48-7.51 (m, 3H), 4.49-4.54 (m, 1H), 3.90-3.94 (m, 1H), 3.24-3.33 (m, 2H), 2.97-3.06 (m, 1H), 2.46 (t, J=7.2 Hz, 2H), 2.17-2.24 (m, 4H), 1.93-1.98 (m, 4H). $t_R$ LCMS 6.0 min. Purity >99%; MS [M+H]$^+$ m/z 368.

5,5,5-trifluoro-1-{4-[3-(4-methanesulfonylphenyl)-1,2,4-oxadiazol-5-yl]piperidin-1-yl}pentan-1-one (46). 5,5,5-Trifluoropentanoic acid (1.3 equiv), EDCI (1.3 equiv), HOBt (0.3 equiv) and diisopropylethylamine (4 equiv) were mixed in DMF (2 mL) for 5 minutes. 4-(3-[4-(methylsulfonyl)phenyl-] 1,2,4-oxadiazol-5-yl]piperidine (34c) (0.85 mmol, 1 equiv) was added with 3 mL of DMF. The reaction mixture was stirred overnight at room temperature and then evaporated under reduced pressure and purified by preparative HPLC. Yield 69%; $^1$H NMR (CD$_2$Cl$_2$) δ 8.32 (d, J=8.7 Hz, 2H), 8.08 (d, J=8.7 Hz, 2H), 4.52-4.57 (m, 1H), 3.92-3.96 (m, 1H), 3.23-3.39 (m, 2H), 3.11 (s, 3H), 2.92-3.01 (m, 1H), 2.46 (t, J=7.2 Hz, 2H), 2.16-2.32 (m, 4H), 1.82-2.01 (m, 4H). $t_R$ LCMS 5.7 min. Purity >99%; MS [M+H]$^+$ m/z 446.

Biology.

EthR-DNA binding assay. SPR analysis of the molecular interactions between EthR and the EthA promoter region was performed using "Research grades Streptavidin-coated Sensor Chips (Sensor Chip SA, Biacore Inc.)" on a BIAcore3000 instrument (Biacore, Uppsala, Sweden). The 106-bp biotinylated DNA fragment overlapping the ethA/ethR intergenic region was obtained by polymerase chain reaction (PCR), purified by agarose gel electrophoresis, and immobilized onto the SA sensor chip. The biotinylated DNA fragment was injected in one channel of the chip at 150 ng/mL to obtain a 75 Resonance Unit (RU) stable fixation to immobilize streptavidin. Another channel of the chip was loaded with a biotinylated double stranded 113-bp long irrelevant DNA fragment (+14 to +127 fragment of the E. coli bla gene PCR amplified using oligonucleotides O-343: TTTCCGTGTCGCCCTTAT-TCC and O-344: CCACTCGTGCACCCAACTGAT, and pUC18 as substrate). Binding of EthR to the immobilized DNA was performed at 25° C. in 10 mM Tris-HCl (pH 7.5), 200 mM NaCl, 0.1 mM EDTA, 1 mM DTT and 1% DMSO at a flow rate of 20 µL/min for 3 min. Specific Interaction (SI) between EthR and the 106-bp DNA fragment was defined as the signal difference between both channels. For dose response curves establishment, the test compounds were serially diluted in the binding buffer containing 590 nM EthR, incubated 5 min at 37° C. then injected in the BIAcore at a flow rate of 20 µL/min for 3 min. SI values were measured at the end of the injection period and used to calculate the inhibition of protein-DNA interaction. IC$_{50}$ values were determined using Graph Pad Prism software.

Intracellular Assay Raw264.7 macrophages (108 cells) were infected with H37Rv-GFP suspension at a MOI of 1:1 in 300 mL for 2 h at 37° C. with shaking (100 rpm). After two washes by centrifugation at 1100 rpm for 5 min, the remaining extracellular bacilli from the infected cells suspension were killed by a 1 h Amykacin (20 µM, Sigma, A2324-5G) treatment. After a final centrifugation step, 40 µL of M. tuberculosis H37Rv-GFP colonized macrophages were dispensed with the Wellmate (Matrix) into 384-well Evotec plates pre-plated with 10 µL of compound mixture diluted in cell medium and incubated for 5 days at 37° C., 5% CO$_2$. Macrophages were then stained with SYTO 60 (Invitrogen, S11342) for 1 h followed by plate sealing. Confocal images were recorded on an automated fluorescent ultra-high-throughput microscope Opera (Evotec). This microscope is based on an inverted microscope architecture that allows imaging of cells cultivated in 96- or 384-well microplates (Evotec). Images were acquired with a 20×-water immersion objective (NA 0.70). A double laser excitation (488-nm and 635-nm) and dedicated dichroic mirrors were used to record green fluorescence of mycobacteria and red fluorescence of the macrophages on two different cameras respectively. A series of four pictures at the center of each well were taken and each image was then processed using dedicated image analysis. The percent of infected cells and the number of cells are the two parameters extracted from images analysis as previously reported. Data of two replicates are average.

Potency assay of test compounds on *M. tuberculosis* (ethionamide concentration fixed at 0.1 µg/mL, serial dilution of test compounds). Ethionamide (Sigma E6005-5G) is diluted into DMSO to 10 mg/mL and aliquots are stored frozen at −20° C. Test compounds are suspended in pure DMSO at a concentration of 40 mg/mL in Matrix tubes and then diluted by a ten-fold dilution to 4 mg/mL in eppendorf tubes. Ten 2-fold serial dilutions of compounds are performed in DMSO in Greiner 384 well V-shape polypropylene plates (Greiner, #781280). Equal volumes (5 µL) of diluted compounds and of ethionamide are transferred to a 384-well low volume polypropylene plate (Corning, #3672). Two independent replicates were done for each setting. On the day of the experiment, 0.5 µL of compound-plate is first transferred by EVOBird platform (Evotec) to cell assay plates pre-plated with 10 µL of assay medium.

ADME studies.

Solubility/Metabolic Stability. These experiments were analyzed using a LC-MS-MS triple-quadrupole system (Varian 1200 ws) under SIM or MRM detection with optimized mass parameters (declustering potential; collision energy and drying gas temperature).

Solubility. The 10 mM solution (40 µL) in DMSO of the sample was added to 1.960 mL of MeOH or PBS at pH 7.4. The samples were gently shaken for 24 h at room temperature, then centrifuged for 5 min, and filtered over 0.45 µm filters. An amount equal to 20 µL of each solution was added to 180 µL of MeOH and analyzed by LC-MS. The solubility was determined by the ratio of mass signal areas PBS/MeOH.

Metabolic stability. We purchased mouse (CD-1) liver microsomes from BD Gentest. We performed all incubations in duplicate in a shaking water bath at 37° C. The incubation mixtures contained 1 µM of compound with 1% methanol used as a vehicle, mouse liver microsomes (0.6 mg of microsomal protein per ml), 5 mM $MgCl_2$, 1 mM NADP, 5 mM glucose-6-phosphate, 0.4 $U·mL^{-1}$ glucose-6-phosphate dehydrogenase and 50 mM potassium phosphate buffer (pH 7.4) in a final volume of 1.5 mL. We took samples at 5, 10, 20, 30 and 40 min after microsome addition, and we stopped the reactions by adding ice-cold acetonitrile containing 1 µM internal standard (four volumes). We centrifuged the samples for 10 min at 10000 g and 4° C. to pellet precipitated microsomal proteins, and we subjected the supernatant to liquid chromatography-tandem mass spectrometry (LC-MS/MS) analysis. We performed control incubations with denaturated microsomes with acetonitrile containing 1 µM internal standard, and we took samples at the start of the incubation and 40 min later (to evaluate the chemical stability of the compounds in the experimental conditions). For LC-MS/MS, we used a Varian HPLC-MS/MS system 1200 L triple quadrupole mass spectrometer equipped with an electrospray ionization source. Analytes were separated in incubation mixtures by HPLC with a Luna C18(2), 5 µm, 50×2.1 mm column (Phenomenex). The mobile phase solvents used were 0.1% formic acid in water (A) or 0.1% formic acid in acetonitrile (B). We applied the following mobile phase gradient: 2-98% (B) for 2.30 min; hold at 98% (B) for 1.00 min; 98-2% (B) for 0.10 min; 2% (B) hold for 1.50 min. The injection volume was 10 µL and the flow rate was 0.6 $mL·min^{-1}$. We quantified each compound by converting the corresponding analyte/internal standard peak area ratios to percentage drug remaining, using the initial ratio values in control incubations as 100%. We used propranolol, known as a high hepatic clearance drug in rodents, as a quality-control compound for the microsomal incubations. Intrinsic clearance was determined based on the following equation:

$$Cl_{int}=(dose/AUC)/\text{Concentration of microsomes and is expressed as } \mu L/min/mg \text{ of proteins.}$$

Formulation. Compounds were dissolved in an aqueous hydroxypropyl-β-cyclodextrin (100 mM) solution to reach a final concentration of 3 mg/mL (upon horizontal shaking in flasks at 37° C. overnight), or in 100% DMSO to reach a final concentration of 14.5 mg/mL.

Pharmacokinetic experiments (DMSO Formulation). Compounds were administered at 20 mg per kg body weight by oral route to Swiss mice (22-24 g) (WIV-ISP breeding). Three mice per time point were anesthetized with ketamine-xyalzine and bled them at 10 min, 20 min, 30 min, 1 h, 2 h, 3 h and 6 h after administration of a single dose of ligands. Blood was collected from the brachial region on lithium heparinated tubes in order to prevent coagulation. The blood samples were centrifuged (5000 g, 15 min) for plasma separation.

Pharmacokinetic experiments (aqueous hydroxypropyl-β-cyclodextrin Formulation). Compounds solubilized in aqueous hydroxypropyl-β-cyclodextrin solution (100 mM) were administered in single dose (20 mg/kg) to CD1 female mice (25-30 g) (Charles River Laboratories). After 10 min, 20 min, 30 min, 1 h, 2 h and 4 h, mice were anesthetized with an intraperitoneal co-administration of ketamine (80 mg/kg) and Domitor (0.8 mg/kg) and blood was sampled from the inferior vena cava. Mice were immediately sacrificed by cervical dislocation. Three mice were dosed per kinetics time point. The blood samples collected on lithium heparinated tubes in order to prevent coagulation were centrifuged (5000 g, 15 min, 4° C.) for plasma separation.

Plasma samples preparation. Plasma samples were thawed on ice. Aliquots of 50 µL were precipitated with 450 µL of ice cold acetonitrile containing internal standard (1 µM). The samples were vigorously mixed with a Vortex, centrifuged at 10000 rpm, at 4° C. for 10 min and the supernatants were transferred into Matrix tubes for LC-MS-MS analysis. Spiked standard solutions (10, 50, 100, 500, 1000, 5000, 10000 and 50000 nM) were prepared the same way.

TABLE 1

Intracellular activities of compounds 3-33.

| Compd | R1 | $EC_{50}$ $(\mu M)^a$ |
|---|---|---|
| 3 | thiophene | 0.1 |
| 4 | thiophene-methylene | 1.3 |

TABLE 1-continued
Intracellular activities of compounds 3-33.
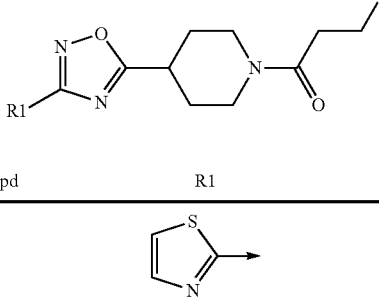
| Compd | R1 | EC$_{50}$ (μM)$^a$ |
|---|---|---|
| 5 | 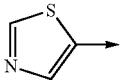 | 0.5 |
| 6 | 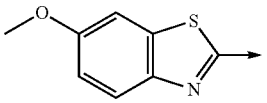 | 2.5 |
| 7 | 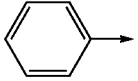 | 0.2 |
| 8 | 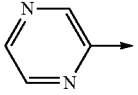 | 0.5 |
| 9 | 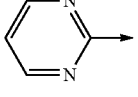 | 20 |
| 10 | 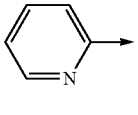 | 9.0 |
| 11 | 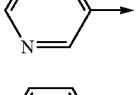 | >10.0 |
| 12 | 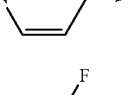 | 4.3 |
| 13 | 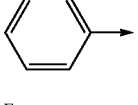 | 9.3 |
| 14 | 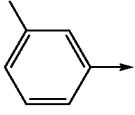 | 10.0 |
| 15 | 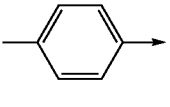 | 1.0 |
| 16 | 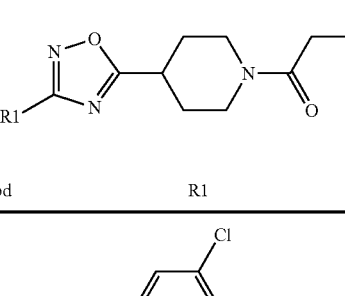 | 7.9 |
TABLE 1-continued
Intracellular activities of compounds 3-33.
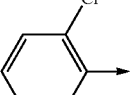
| Compd | R1 | EC$_{50}$ (μM)$^a$ |
|---|---|---|
| 17 | 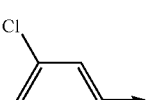 | 6.3 |
| 18 | 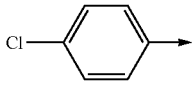 | 10.0 |
| 19 | 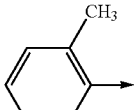 | 1.1 |
| 20 | 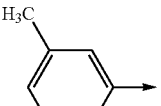 | 1.2 |
| 21 | 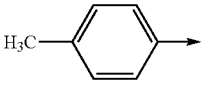 | 2.3 |
| 22 | 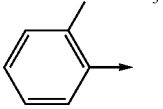 | 2.2 |
| 23 | 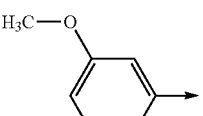 | >10.0 |
| 24 | 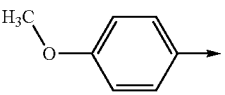 | 10.0 |
| 25 | 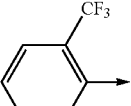 | >10.0 |
| 26 |  | >10.0 |

TABLE 1-continued

Intracellular activities of compounds 3-33.

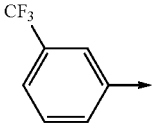

| Compd | R1 | EC$_{50}$ (μM)$^a$ |
|---|---|---|
| 27 | 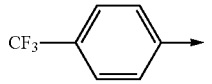 | >10.0 |
| 28 | 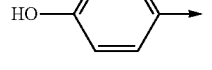 | 2.5 |
| 29 | 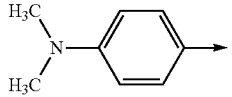 | 10.0 |
| 30 | 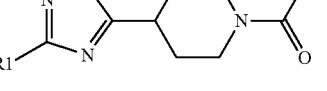 | 10.0 |
| 31 | 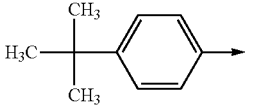 | >10.0 |
| 32 | 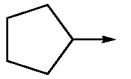 | 0.8 |
| 033 | 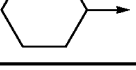 | 4.0 |

EC$_{50}$ represents the concentration of ligand that allows ethionamide at 0.1 μg/mL (normal MIC/10) to inhibit 50% of *M. tuberculosis* growth in macrophages, EC$_{50}$ are mean of two experiments. SD was <10% in most cases.

TABLE 2

Biological activities, physicochemical properties, mouse microsomal stability and PK parameters of compounds 2, 3, 5, 7, 8, 41-46.

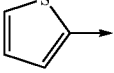

| | Structure | | | Biological activity | | Physico-chemical properties | Mouse microsomal stability | PK |
|---|---|---|---|---|---|---|---|---|
| Cpd | R1 | n | m | EC$_{50}$ (μM)$^a$ | IC$_{50}$ (μM)$^b$ | Solubility$^c$ (μg/mL) | CL$_{int}$ (μL/min/mg)$^d$ | AUC$_\infty$ (μg·ml$^{-1}$·h) |
| 2 | 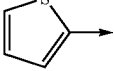 | 1 | 1 | 0.4 | 2.0 | 80 | 4 | 0.1$^e$ |
| 3 | 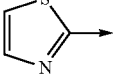 | 2 | 1 | 0.1 | 1.6 | 150 | 213 | — |
| 5 | 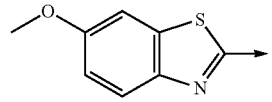 | 2 | 1 | 0.5 | 2.8 | 300 | 37 | 73.5$^e$ 100.5$^f$ |
| 7 |  | 2 | 1 | 0.2 | 1.0 | 6 | 197 | — |

TABLE 2-continued

Biological activities, physicochemical properties, mouse microsomal stability and PK parameters of compounds 2, 3, 5, 7, 8, 41-46.

| | Structure | | | Biological activity | | Physicochemical properties | Mouse microsomal stability | PK |
|---|---|---|---|---|---|---|---|---|
| Cpd | R1 | n | m | $EC_{50}$ ($\mu M$)[a] | $IC_{50}$ ($\mu M$)[b] | Solubility[c] ($\mu g/mL$) | $CL_{int}$ ($\mu L/min/mg$)[d] | $AUC_\infty$ ($\mu g \cdot ml^{-1} \cdot h$) |
| 8 | phenyl | 2 | 1 | 0.5 | 9.1 | 40 | — | — |
| 41 | thiazol-2-yl | 1 | 1 | 6.3 | — | — | — | — |
| 42 | thiazol-2-yl | 2 | 2 | 0.06 | 0.4 | 410 | 15 | 98.6[f] |
| 43 | thien-2-yl | 1 | 2 | 0.1 | — | 237 | 297 | — |
| 44 | thien-2-yl | 2 | 2 | 0.07 | — | — | — | — |
| 45 | phenyl | 2 | 2 | 0.1 | — | 80 | 73 | — |
| 46 | 4-(methylsulfonyl)phenyl | 2 | 2 | 0.02 | — | 80 | 14 | — |

$EC_{50}$ represents the concentration of ligand that allows ethionamide at 0.1 µg/mL (normal MIC/10) to inhibit 50% of *M. tuberculosis* growth in macrophages. [b]$IC_{50}$ represents the concentration of ligand that inhibits 50% of the interaction of EthR with its promoter. [c]Solubilities were determined at pH 7.4. [d]Propranolol known as a high hepatic clearance drug in rodents was used as reference for microsomal incubations ($CL_{int}$=121 µL/min/mg). [e]dose: 20 mg/kg, vehicle: 100% DMSO. [f]dose: 20 mg/kg, vehicle: aqueous solution of 100 mM hydroxypropyl-β-cyclodextrin-based formulation. See Experimental Section for further details on all assays.

Abbreviations: ACM, automated confocal microscopy; AcOEt, ethyl acetate; AcOH, acetic acid; AUC, Area under the concentration-time curve; Boc, t-butoxycarbonyl; $CH_3CN$, acetonitrile; DCM, dichloromethane; DIEA, diisopropylethylamine; DMF, dimethylformamide; DMSO, dimethylsulfoxide; DOTS, directly observed treatment short-course; EDCI, N-ethyl-3-(3-dimethylaminopropyl)-carbodiimide; ETH, ethionamide; $Et_3N$, triethylamine; EtOH, ethanol; GFP, green fluorescent protein; HBTU, 0-benzotriazole-N,N,N',N'-tetramethyluronium hexafluorophosphate; HOBt, N-hydroxybenzotriazole; MDR-TB, multi-drug resistant tuberculosis; MeOH, methanol; MIC, minimal inhibitory concentration; PBS, phosphate buffered saline; PK, pharmacokinetic; RT, room temperature; SAR, structure-activity relationships; SPR, surface plasmon resonance; TB, tuberculosis; TEA, triethylamine; THF, tetrahydrofuran; XDR-TB, extensively drug resistant tuberculosis.

The invention claimed is:
1. A compound of Formula (I)

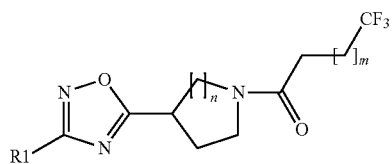

wherein R1 is chosen among the following radicals:

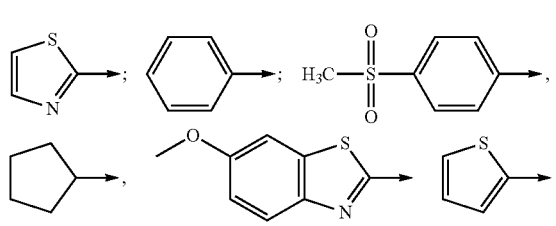

and n=2 or 1 and m=2 or 1 with the proviso that m=2 when R1 is

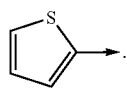

2. The compound according to claim 1 wherein n=2.
3. The compound according to claim 1, wherein m=2.
4. The compound according to claim 1, wherein R1 is chosen among

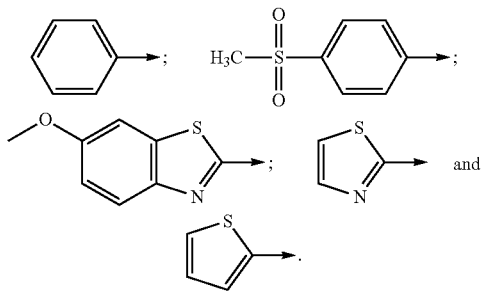

5. The compound according to claim 1, wherein R1 is chosen among

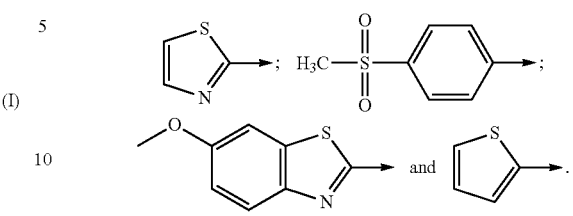

6. The compound according to claim 1, wherein R1 is chosen among

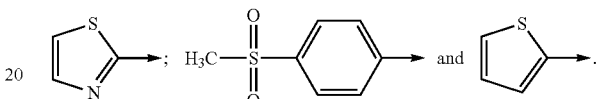

7. The compound according to claim 1, wherein R1 is Or

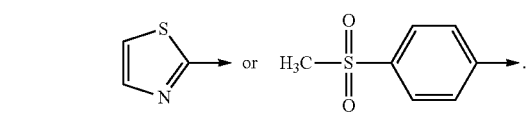

8. A pharmaceutical composition comprising, as an active compound, at least one compound according to claim 1 and a pharmaceutically acceptable excipient.
9. A pharmaceutical composition according to claim 8, further comprising at least one antibiotic chosen from antibiotics that are activable via the EthA enzymatic pathway.
10. A pharmaceutical composition according to claim 9, wherein said antibiotic is chosen among ethionamide, prothionamide, isoxyl and thiacetazone.
11. A pharmaceutical composition according to claim 8, wherein said composition is adapted for an oral administration.
12. A method of treatment of tuberculosis comprising administering to a patient in need thereof an effective amount of a compound according to claim 1.
13. A method of treatment of tuberculosis comprising administering simultaneously, separately or sequentially to a patient in need thereof an effective amount of a compound according to claim 1 and at least one antibiotic chosen among antibiotics activable via the EthA enzymatic pathway.
14. The method of claim 13 wherein the antibiotic activable via the EthA enzymatic pathway is chosen among ethionamide, prothionamide, isoxyl and thiacetazone.

* * * * *